United States Patent
Feng et al.

(10) Patent No.: US 8,124,060 B2
(45) Date of Patent: Feb. 28, 2012

(54) COMPOSITIONS CONTAINING A BIMODAL FILM FORMER AND CROSS-LINKED STARCH

(75) Inventors: Sue Feng, Edison, NJ (US); Karen Yung, New York, NY (US)

(73) Assignee: L'Oreal S.A., Paris (FR)

( * ) Notice: Subject to any disclaimer, the term of this patent is extended or adjusted under 35 U.S.C. 154(b) by 1269 days.

(21) Appl. No.: 11/676,759

(22) Filed: Feb. 20, 2007

(65) Prior Publication Data

US 2008/0199415 A1    Aug. 21, 2008

(51) Int. Cl.
*A61K 8/81* (2006.01)
*A61K 8/60* (2006.01)
*A61Q 1/12* (2006.01)

(52) U.S. Cl. .................. 424/69; 424/70.1; 424/70.7

(58) Field of Classification Search .................. None
See application file for complete search history.

(56) References Cited

U.S. PATENT DOCUMENTS 5,985,258 A * 11/1999 Alwattari et al. ............ 424/70.7
(Continued)

FOREIGN PATENT DOCUMENTS

WO    WO 2005/087191    9/2005
(Continued)

OTHER PUBLICATIONS

Interpolymer, Syntran PC 5100, Bimodal Polymer Technology, retrieved online on Jul. 27, 2010, pp. 1-3, Jan. 25, 2005.*

(Continued)

*Primary Examiner* — Tracy Vivlemore
*Assistant Examiner* — Jennifer Berrios
(74) *Attorney, Agent, or Firm* — Oblon, Spivak, McClelland, Maier & Neustadt, L.L.P.

(57) ABSTRACT

The invention relates to compositions containing (a) at least one bimodal film former; and (b) at least one cross-linked starch as well as to methods of using such compositions and kits containing such compositions.

17 Claims, No Drawings

U.S. PATENT DOCUMENTS

| | | | |
|---|---|---|---|
| 6,248,336 B1 | 6/2001 | McDermott | |
| 6,248,338 B1 | 6/2001 | Müller et al. | |
| 6,503,495 B1 | 1/2003 | Alwattari et al. | |
| 2002/0187116 A1* | 12/2002 | De La Poterie | 424/63 |
| 2003/0003301 A1* | 1/2003 | Whitney et al. | 428/403 |
| 2004/0234486 A1 | 11/2004 | Hashimoto | |
| 2005/0095213 A1* | 5/2005 | Blin et al. | 424/70.11 |

FOREIGN PATENT DOCUMENTS

| | | |
|---|---|---|
| WO | WO 2006/028931 | 3/2006 |

OTHER PUBLICATIONS

Cosmetics Hair Care, Bimodal Polymers, SÖWF-Journal, pp. 62, 64, 66-68 Dec. 2004, 130.

Interpolyrner, Bimodal Polymer Technology, Improving Hair Styling Products, 2 pages, 2005, Interpolymer Corporation.

Interpolymer, Consumer Specialties Technology, Bimodals, Bimodal Polymer Technology, Improving Hair and Skin Care Products, 4 pages.

Interpolymer, Syntran PC 5117, Bimodal Polymer Technology, 3 pages.

Interpolymer, Syntran PC 5100, Bimodal Polymer Technology, 3 pages.

Interpolymer, Syntran PC 5107, Bimodal Polymer Technology, 4 Pages.

Interpolymer, Syntran PC 5112, Bimodal Polymer Technology, 4 pages.

L. Marlier, M. Selter, Bimodal Polymers for Next Generation Hair Styling Products, SÖFW-Journal, 130, Dec. 2004.

National Starch Personal Care, Structure XL (28-030A) Hydroxylpropyl Starch Phosphate, 3 pages, pdf.07.18.2002.

* cited by examiner

COMPOSITIONS CONTAINING A BIMODAL FILM FORMER AND CROSS-LINKED STARCH

FIELD OF THE INVENTION

The present invention generally relates to compositions comprising at least one cross-linked starch and at least one bimodal film former as well as to methods of applying such compositions to keratin materials and kits comprising such compositions. Such compositions possess improved properties and characteristics such as, for example, providing increased adherence of larger particles such as glitter to the keratin materials, particularly hair and eyelashes, and providing improved curl and/or lift to eyelashes without clumping and/or balling.

DISCUSSION OF THE BACKGROUND

Cosmetic compositions often contain large particles like glitter. In the past, adhering larger particles such as glitter to the keratin materials, particularly hair and eyelashes, has been problematic. Thus, there is a need for improved large particle-containing compositions in which the large particles, like glitter, adhere well to keratin materials.

Also, compositions for application to eyelashes such as mascaras often have problems with clumping or balling upon application owing primarily to the presence of large amounts of wax in these compositions. Thus, there is also a need for improved compositions for application to eyelashes which possess desirable properties upon application such as improved curl and/or lift of the eyelashes but which possess decreased undesirable characteristics such as clumping and/or balling.

Accordingly, one aspect of the present invention is a care and/or makeup and/or treatment composition for keratin materials such as eyelashes which is able to address or overcome some or all of the aforementioned problems with the prior art compositions.

SUMMARY OF THE INVENTION

The present invention relates to compositions, particularly cosmetic compositions for eyelashes such as mascaras, topcoats and basecoats, comprising (a) at least one bimodal film former; and (b) at least one cross-linked starch.

The present invention also relates to compositions, particularly cosmetic compositions for eyelashes such as mascaras, topcoats and basecoats, comprising (a) at least one bimodal film former; and (b) at least one cross-linked starch, wherein the composition is substantially wax-free or wax-free.

The present invention also relates to compositions, particularly cosmetic compositions for eyelashes such as mascaras, topcoats and basecoats, comprising (a) at least one bimodal film former; (b) at least one cross-linked starch; and (c) glitter. Such compositions can optionally be substantially wax-free or wax-free.

The present invention also relates to compositions, particularly cosmetic compositions for eyelashes such as mascaras, topcoats and basecoats, comprising (a) at least about 50% by weight of at least one bimodal film former; and (b) at least one cross-linked starch. Such compositions can optionally be substantially wax-free or wax-free.

The present invention also relates to methods of dispersing particles such as glitter in a composition comprising combining the particles with at least one cross-linked starch and at least one bimodal polymer.

The present invention further relates to methods of adhering particles such as glitter to keratin materials such as eyelashes or hair comprising applying a composition comprising at least one particle, at least one cross-linked starch and at least one bimodal polymer to the keratin material.

The present invention also relates to methods of curling and/or lifting eyelashes comprising applying a composition comprising at least one cross-linked starch and at least one bimodal polymer to the eyelashes in an amount sufficient to curl and/or lift the eyelash.

The present invention further relates to methods of producing a composition such as, for example, a mascara composition at or about room temperature comprising combining at least one cross-linked starch and at least one bimodal film forming agent.

The present invention also relates to methods of treating, caring for, making up or enhancing the appearance of keratin materials comprising applying compositions of the present invention to the keratin materials in an amount sufficient to treat, care for, make-up and/or enhance the appearance of the keratin materials.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

"Cosmetically acceptable" means that the item in question is compatible with any keratin material. For example, "cosmetically acceptable medium" means a medium that is compatible with any keratin material.

"Keratin material" includes, for example, skin, hair, nails, eyelashes, eyebrows, lips and any other area of body or facial skin.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human lips followed by "kissing" a material, for example, a sheet of paper, after expiration of a certain amount of time following application, such as 2 minutes after application. Similarly, transfer resistance of a composition may be evaluated by the amount of product transferred from a wearer to any other substrate, such as transfer from the neck of an individual to a collar after the expiration of a certain amount of time following application. The amount of composition transferred to the substrate (e.g., collar, or paper) may then be evaluated and compared. For example, a composition may be transfer resistant if a majority of the product is left on the wearer, e.g., lips, neck, etc. Further, the amount transferred may be compared with that transferred by other compositions, such as commercially available compositions.

"Long wear" compositions as used herein, refers to compositions where at least one property chosen from consistency, texture, and color remains the same as at the time of application, as viewed by the naked eye, after an extended period of time, such as, for example, 1 hour, 2 hours, and further such as 8 hours. Long wear properties may be evaluated by any method known in the art for evaluating such properties. For example, long wear may be evaluated by a test involving the application of a composition to human skin (including lips) and evaluating the consistency, texture and color of the composition after an extended period of time. For example, the consistency, texture and color of a lip composition may be evaluated immediately following application and these characteristics may then be re-evaluated and compared after an individual has worn the lip composition for a certain amount of time. Further, these characteristics may be evaluated with respect to other compositions, such as commercially available compositions.

"Waterproof" as used herein refers to the ability to repel water and permanence with respect to water. Waterproof properties may be evaluated by any method known in the art for evaluating such properties. For example, a mascara composition may be applied to false eyelashes, which may then be placed in water for a certain amount of time, such as, for example, 20 minutes. Upon expiration of the pre-ascertained amount of time, the false eyelashes may be removed from the water and passed over a material, such as, for example, a sheet of paper. The extent of residue left on the material may then be evaluated and compared with other compositions, such as, for example, commercially available compositions. Similarly, for example, a composition may be applied to skin, and the skin may be submerged in water for a certain amount of time. The amount of composition remaining on the skin after the pre-ascertained amount of time may then be evaluated and compared. For example, a composition may be waterproof if a majority of the product is left on the wearer, e.g., eyelashes, skin, etc.

"Tackiness" as used herein refers to the adhesion between two substances. For example, the more tackiness there is between two substances, the more adhesion there is between the substances. To quantify "tackiness," it is useful to determine the "work of adhesion" as defined by IUPAC associated with the two substances. Generally speaking, the work of adhesion measures the amount of work necessary to separate two substances. Thus, the greater the work of adhesion associated with two substances, the greater the adhesion there is between the substances, meaning the greater the tackiness is between the two substances.

Work of adhesion and, thus, tackiness, can be quantified using acceptable techniques and methods generally used to measure adhesion, and is typically reported in units of force time (for example, gram seconds ("g s")). For example, the TA-XT2 from Stable Micro Systems, Ltd. can be used to determine adhesion following the procedures set forth in the TA-XT2 Application Study (ref: MATI/PO.25), revised January 2000, the entire contents of which are hereby incorporated by reference. According to this method, desirable values for work of adhesion for substantially non-tacky substances include less than about 0.5 g s, less than about 0.4 g s, less than about 0.3 g s and less than about 0.2 g s. As known in the art, other similar methods can be used on other similar analytical devices to determine adhesion.

The compositions, methods and kits of the present invention can comprise, consist of, or consist essentially of the essential elements and limitations of the invention described herein, as well as any additional or optional ingredients, components, or limitations described herein or any otherwise useful ingredient found in personal care compositions intended for application to keratin materials.

The composition of the present invention may be in any form suitable for use on keratin materials such as, for example, non-solid anhydrous, oil-free or emulsion compositions (for example, water-in-oil emulsion, oil-in-water emulsion, multiple emulsion (W/O/W or O/W/O), nanoemulsions, etc.). The compositions of the present invention can be a mascara, eyeliner or eyeshadow. Generally speaking, mascaras contain colorants such as pigments. The compositions of the present invention can be used as a basecoat and/or topcoat for application beneath and/or onto other products applied to keratin materials such as eyelashes.

As defined herein, stability is tested by placing the composition in a controlled environment chamber for 8 weeks at 25° C. In this test, the physical condition of the sample is inspected as it is placed in the chamber. The sample is then inspected again at 24 hours, 3 days, 1 week, 2 weeks, 4 weeks and 8 weeks. At each inspection, the sample is examined for abnormalities in the composition such as phase separation if the composition is in the form of an emulsion. The stability is further tested by repeating the 8-week test at 4° C., 37° C., 45° C. and/or under freeze-thaw conditions. A composition is considered to lack stability if in any of these tests an abnormality that impedes functioning of the composition is observed. The skilled artisan will readily recognize an abnormality that impedes functioning of a composition based on the intended application.

Bimodal Film Former

According to the present invention, compositions comprising at least one bimodal film forming agent (film former) are provided. According to preferred embodiments, the bimodal film forming agent forms a bimodal interpenetrating network containing multiple functionalities (for example, cationic and anionic functionalities) which is reversibly cross-linked at least partially through the multiple functionalities. Exemplary bimodal film forming agents are disclosed in PCT patent application nos. WO 05/087191 and WO 06/028931, and corresponding U.S. provisional application Nos. 60/551,658, 60/606,985, and 60/627,224, the entire contents of all of which are hereby incorporated by reference in their entirety.

Suitable bimodal film forming agents include, but are not limited to, film forming agents having both cationic and anionic functionalities. According to particularly preferred embodiments of the present invention, the bimodal film forming agent comprises at least one acrylic acid-based, (meth) acrylic acid-based, acrylate-based or (meth)acrylate-based monomer having anionic and/or cationic functionalities. Suitable polymers or copolymers include, but are not limited to, polymers comprising polyacrylates such as those identified in the *International Cosmetic Ingredient Dictionary and Handbook* ($9^{th}$ ed. 2002) such as, for example, polyacrylate-1, polyacrylate-2, polyacrylate-3, polyacrylate-4 . . . polyacrylate-16, polyacrylate-17, polyacrylate-18, polyacrylate-19 . . . , etc. Such (co)polymers, or similar (co)polymers, can be combined individually or with other (co)polymers in such a way to form suitable bimodal film forming agents having both cationic and anionic functionalities.

According to particularly preferred embodiments, the bimodal film forming agent is selected from the group consisting of polymers consisting of polyacrylate-21 and acrylates/dimethylaminoethyl methacrylate copolymer (marketed under the name Syntran PC 5100 by Interpolymer), polyacrylate-16 (marketed under the name Syntran PC 5112 by Interpolymer), polyacrylate-18 and polyacrylate-19 (marketed under the name Syntran PC 5107 by Interpolymer), and polyacrylate-18 and polyacrylate-19 (marketed under the name Syntran PC 5117 by Interpolymer). The bimodal film forming agent containing polyacrylate-21 and acrylates/dimethylaminoethylmethacrylate copolymer (Syntran PC 5100) and polyacrylate-16 (Syntran PC 5112) are particularly preferred.

Preferably, the bimodal film forming agent is present in an amount ranging from about 15% to about 80% by weight of the total weight of the composition, more preferably from about 30% to about 70% of the total weight of the composition, more preferably from about 50% to about 70% of the total weight of the composition, and most preferably from about 50% to about 65%, including all ranges and subranges therebetween.

Cross-Linked Starch

According to the present invention, compositions comprising at least one cross-linked starch are provided. Suitable cross-linked starch compounds are disclosed in U.S. patent application publication no. 2004/0234486 and U.S. Pat. No. 6,248,338, the entire contents of both of which are herein incorporated by reference.

According to preferred embodiments, "cross-linked starch" refers to cross-linked starch products in which specific modified starches are cross-linked between the same types of starches or between different types of starches. Preferably, the at least one cross-linked starch is selected from the group consisting of a cross-linked product of a hydroxyalkyl modified starch with a carbon number of 2 to 5, a cross-linked product of a hydroxyalkyl modified starch with a carbon number of 2 to 5 and an acyl modified starch with a carbon number of 2 to 18, and a cross-linked product of an acyl modified starch with a carbon number of 2 to 18. Such starches can be used alone or in combination.

"Hydroxyalkyl modified starch with a carbon number of 2 to 5" refers to starches in which a hydroxyl group is bonded with the starch backbone via an alkyl group having a carbon number of C2 to C5, and which provide a suitable balance between hydrophilicity and lipophilicity. The position of the hydroxyl group in the alkyl group is not of decisive importance, and may be any given position. The substitution degree by the hydroxyalkylation is preferably 0.08 to 0.3. "Substitution degree" refers to an average number of hydroxyl groups of a starch molecule per anhydroglucol-unit. The hydroxyalkylation of a natural starch can be achieved by reacting a natural starch with alkene oxide having only an appropriate number of carbon atoms of the natural starch. A hydroxyethylated starch and/or a hydroxypropylated starch that can be obtained by reacting a starch with ethylene oxide or propylene oxide are particularly preferable. In addition, these may have a plurality of hydroxyl groups per alkyl group.

"Acyl modified starch with a carbon number of 2 to 18" refers to starches that are acylated by an acyl group with a carbon number of 2 to 18, which provide a suitable balance between hydrophilicity and lipophilicity. In general, the acylation is performed by reacting a starch with an acid anhydride represented by the general formula $(RCO)_2O$, where R is an alkyl group such as a methyl group or an ethyl group.

The cross-linking of these modified starches can be achieved with suitable cross-linking agents, that is, bifunctional compounds. Examples of preferred cross-linking methods include phosphorylation. In this case, the starches are reacted with phosphoryl chloride, phosphorus pentoxide and/or sodium trimetaphosphate. The two starches are cross-liked by an anion P—O radical.

Further examples of preferred cross-linking methods include methods using alkanedicarboxylic acid or alkenedicarboxylic acid with a carbon number of C4 to C18. It is preferable to use alkanedicarboxylic acid with a carbon number of C4 to C8, particularly, adipic acid. Alkanedicarboxylic acid or alkenedicarboxylic acid with a carbon number of C4 to C18 provides a bonding between the two starches via an ester bound. The starches may be either linear or branched. A cross-linked product that is cross-linked by such dicarboxylic acid can be obtained by, for example, reacting the starch with a mixed anhydride of dicarboxylic acid and acetic acid. In the case of a dry starch, a cross-linking agent is generally used in an amount less than 0.1 wt %, and, normally, less than 0.6 wt %.

The starting starches used for obtaining the above-described specific starches may be any vegetable starches. Examples of such starting starches include corn, potato, wheat, rice, tapioca, sweet potato and sago. These starting starches preferably have an amylopectin content of at least 70 wt %, more preferably, at least 85 wt %, and most preferably, at least 90 wt %.

According to particularly preferred embodiments of the present invention, the cross-linked starch is hydroxypropyl starch phosphate (marketed by National Starch under the name Structure XL).

Preferably, the cross-lined starch is present in an amount ranging from about 1% to about 15% by weight of the total weight of the composition, more preferably from about 2% to about 10% of the total weight of the composition, more preferably from about 3% to about 9% of the total weight of the composition, and most preferably from about 4% to about 8%, including all ranges and subranges therebetween.

According to particularly preferred embodiments, the ratio of bimodal film forming agent to cross-linked starch is at least about 5:1, at least about 7:1, at least about 10:1, at least about 15:1, or at least about 20:1.

Particles

According to preferred embodiments of the present invention, compositions comprising at least one bimodal film forming agent, at least one cross-linked starch, and particles are provided. Suitable particles include, but are not limited to, fibers, glitter, and mixtures thereof.

"Glitter" is material which produces/emits flashes of light and, thus, appears to sparkle. Typically, glitter comprises a plurality of particles (i.e., pieces or fragments of a material) having a regular or irregular periphery, which reflects or refracts light. Materials useful as glitter include particles of metal (e.g., aluminum, copper, silver, gold, and brass), particles of transparent or colored, solid organic materials (e.g., polyethylene terephthalate, polymethacrylate, and polyvinylbutyral), and particles of metal coated film or paper (e.g., aluminum coated polyethylene terephthalate film). Glitter may be clear and/or be provided in a variety of colors (e.g., silver, gold, blue, red, etc.), or mixtures thereof; and may be provided in a variety of shapes (e.g., circles, squares, rectangles, triangles, diamonds, stars, symbols, alphanumerics (i.e., letters and/clor numbers), or mixtures of different shapes.

"Glitter" also includes coated glitter (glitter optionally containing additional colorant which is coated with a suitable coating agent). Such coated glitter can contain any suitable glitter material or any suitable mixture of glitter materials. For example, the glitter may comprise a metal, an organic material, or mixtures thereof. A particularly preferred metal is aluminum, and a particularly preferred organic material is polyethylene terephthalate. Preferably, the coated glitter comprises colorant. Any suitable, cosmetically acceptable colorant can be used. A particularly preferred colorant is D&C Black No. 2 (CI 77266).

Any suitable coating material can be used as long as the material is cosmetically acceptable and forms an acceptable coating on or around the glitter. Preferably, the coating material is a film forming agent (film former). According to preferred embodiments, the coating material comprises a polyurethane compound. Polyurethane compounds are well-known compounds which, generally speaking, are produced by reacting a polyol with a diisocyanate or a polymeric isocyanate. Any polyurethane compound which is capable of forming a coating on or around glitter material and which is cosmetically acceptable can be used. For example, suitable polyurethane compounds include, but are not limited to, polyurethane-1, polyurethane-2, polyurethane-3, polyurethane-4, polyurethane-5, polyurethane-6, polyurethane-7, polyurethane-8, polyurethane-9, polyurethane-10, polyurethane-11, polyurethane-12, polyurethane-13, polyurethane-14, polyurethane-15, polyurethane-16, polyurethane-17, polyurethane-18, polyurethane-19 and polyurethane-20. Polyurethane-11 is particularly preferred.

According to preferred embodiments, the glitter coating comprises at least some of the colorant. Most preferably, the glitter coating contains essentially all of the colorant (that is, 95% or more of the colorant) or all of the colorant.

A particularly preferred example of coated glitter comprising colorant is CosmetaGem which is commercially available from Glitterex. CosmetaGem is polyethylene terephthalate coated with polyurethane-11 in which D&C Black No. 2 has been dispersed.

"Fiber" should be understood as meaning an object of length L and diameter D such that L is very much greater (>>) than D, D being the diameter of the circle in which the cross section of the fiber is inscribed. In particular, the ratio L/D (or shape factor) is chosen in the range extending from about 3.5 to about 2500, preferably from about 5 to about 500 and, better still, from about 5 to about 150.

Suitable fibers include fibers of synthetic or natural, mineral or organic origin. They may be short or long, individual or organized, for example, plaited hollow or solid. These fibers, as long as they satisfy the L/D relationship described above, can have any shape and, in particular, a circular or polygonal, e.g., square, hexagonal or octagonal, cross section depending on the specific application envisaged. Preferably, their ends are blunt and/or smooth to prevent injury.

Preferably, the fibers have a length ranging from about 1 nm to about 20 mm, more preferably from about 10 nm to about 5 mm and, better still, from about 0.1 mm to about 1.5 mm. Their cross section can be within a circle of diameter ranging from about 2 nm to about 100 microns, preferably ranging from about 20 nm to about 20 microns and, better still, from about 500 nm to about 20 microns. The weight or yarn count of the fibers is often given in denier or decitex and represents the weight in grams per 9 km of yarn. Preferably, the fibers according to the invention have a yarn count chosen in the range extending from about 0.15 to about 30 deniers and, better still, from about 0.18 to about 18 deniers.

Specific examples of suitable fibers include, but are not limited to, those used in the manufacture of textiles and, in particular, silk fiber, cotton fiber, wool fiber, flax fiber, cellulose fibers extracted, in particular, from wood, from plants or from algae, polyamide (NYLON®) fiber, rayon fiber, viscose fiber, acetate fiber, in particular, rayon acetate fiber, cellulose fiber or silk fiber, poly-p-phenylene terephthamide fiber, especially KEVLAR®, acrylic fiber, in particular, polymethyl methacrylate fiber or poly(2-hydroxyethyl methacrylate) fiber, polyolefin fiber, and, in particular, polyethylene or polypropylene fiber, glass fiber, silica fiber, aramide fiber, carbon fiber, especially in graphite form, polytetrafluoroethylene TEFLON® fiber, insoluble collagen fiber, polyester fiber, polyvinyl chloride or polyvinylidene chloride fiber, polyvinyl alcohol fiber, polyacrylonitrile fiber, chitosan fiber, polyurethane fiber, polyethylene phthalate fiber, or fibers formed from a mixture of polymers, such as those mentioned above, for instance, polyamide/polyester fibers.

Suitable fibers further include fibers used in surgery, such as resorbable synthetic fibers prepared from glycolic acid and ε-caprolactone, e.g., Monocryl from Johnson & Johnson; resorbable synthetic fibers such the copolymer of lactic acid and glycolic acid, e.g., Vicryl from Johnson & Johnson; terephthalic polyester fibers, e.g., Ethibond from Johnson & Johnson; and stainless steel threads, e.g., Acier from Johnson & Johnson, in particular, for use in nail varnishes.

Moreover, the fibers can be coated or uncoated and surface-treated or otherwise. Examples of coated fibers that can be used in the invention include polyamide fibers coated with copper sulphide for an antistatic effect, for example, R-STAT from Rhodia, or another polymer allowing a particular organization of the fibers (specific surface treatment) or surface treatment which induces color/hologram effects, for example, Lurex fiber from Sildorex.

In accordance with these preferred embodiments of the present invention, the total amount of particles preferably ranges from about 0.1% to about 40% by weight with respect to the total weight of the composition, more preferably from about 1% to about 30% of the total weight of the composition, more preferably from about 2% to about 25% of the total weight of the composition, and most preferably from about 5% to about 20%, including all ranges and subranges therebetween.

Additional Ingredients

The compositions of the present invention can also comprise any additive usually used in cosmetic or dermatologic compositions. For example, waxes, film forming agents, dispersants, antioxidants, oils, preserving agents, fragrances, fillers, neutralizing agents, cosmetic and dermatological active agents such as, for example, emollients, moisturizers, vitamins, anti-wrinkle agents, essential fatty acids, and sunscreens, and mixtures thereof can be added. A non-exhaustive listing of such ingredients can be found in U.S. patent application Ser. No. 10/733,467, filed Dec. 12, 2003, the entire contents of which is hereby incorporated by reference. Further examples of suitable additional components can be found in the other references which have been incorporated by reference in this application. Still further examples of such additional ingredients may be found in the *International Cosmetic Ingredient Dictionary and Handbook* ($9^{th}$ ed. 2002).

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%) relative to the total weight of the composition and further such as from 0.1% to 50% (if present), including all ranges and subranges therebetween.

Needless to say, the composition of the invention should be cosmetically or dermatologically acceptable, i.e., it should contain a non-toxic physiologically acceptable medium and should be able to be applied to the eyelashes of human beings.

Specific examples of additional ingredients include oils, particularly if the composition is an anhydrous composition or an emulsion. Any oils can be used in accordance with the present invention. The oils can be volatile or non-volatile, silicone-based and/or hydrocarbon-based, etc. Thus, for example, the external oil phase may contain, independently or in combination, volatile silicone oils, non-volatile silicone oils, volatile non-silicone oils and non-volatile non-silicone oils.

In one embodiment, the compositions of the present invention are substantially free of silicone oils (i.e., contain less than about 1% of silicone oil). In another embodiment, the compositions are substantially free of non-silicone oils (i.e., contain less than about 1% of non-silicone oil). In another embodiment, the compositions are substantially free of non-volatile oils (i.e., contain less than about 1% of non-volatile oil). In yet another embodiment, the compositions are substantially free of volatile oils (i.e., contain less than about 1% of volatile oil).

Water, when present, preferably represents from about 1% to about 70% by weight of the total weight of the composition, more preferably from about 5% to about 60% of the total weight of the composition, and most preferably from about 10% to about 50%, including all ranges and subranges therebetween.

The compositions may also optionally comprise at least one non-glitter coloring agent. Suitable non-glitter coloring agents include but are not limited to pigments, dyes, such as liposoluble dyes, and nacreous pigments.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow. The liposoluble dyes, when present, generally have a concentration ranging up to 20% by weight of the total weight of the composition, such as from 0.0001% to 6%, including all ranges and subranges therebetween.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, be present in the composition in a concentration ranging up to 50% by weight of the total weight of the composition, such as from 0.1% to 20%, preferably from 0.1% to 15%, including all ranges and subranges therebetween.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

If present, the pigments may be present in the composition in a concentration ranging up to 50% by weight of the total weight of the composition, such as from 0.5% to 40%, and further such as from 2% to 30%, including all ranges and subranges therebetween. In the case of certain products, the pigments, including nacreous pigments, may, for example, represent up to 50% by weight of the composition.

According to particularly preferred embodiments, the compositions of the present invention are substantially free of waxes (i.e., contain less than about 1% of waxes) or free of waxes (i.e., contain less than about 0.1% of waxes).

According to preferred embodiments of the present invention, methods of dispersing particles such as glitter in a composition comprising combining the particles with at least one cross-linked starch and at least one bimodal polymer are provided. In accordance with these embodiments, the at least one cross-linked starch and the at least one bimodal polymers are, together, present in an amount sufficient to disperse the particles in a cosmetically acceptable carrier.

According to other embodiments of the present invention, methods of adhering particles such as glitter or fibers to keratin materials such as eyelashes or hair comprising applying a composition comprising at least one particle, at least one cross-linked starch and at least one bimodal polymer to the keratin material are provided. In accordance with these embodiments, the at least one bimodal polymer and the at least one cross-linked starch are, together, present in an amount sufficient to adhere the particles to the keratin material for at least one hour under standard use conditions, preferably for at least two hours, more preferably for at least 4 hours and most preferably for at least eight hours.

According to yet other embodiments of the present invention, methods of curling and/or lifting eyelashes comprising applying a composition comprising at least one cross-linked starch and at least one bimodal polymer to the eyelashes in an amount sufficient to curl and/or lift the eyelash are provided. In accordance with these embodiments, the at least one bimodal polymer and the at least one cross-linked starch are, together, present in an amount sufficient to curl and/or lift the eyelashes.

According to still other embodiments of the present invention, methods of treating, caring for, making up or enhancing the appearance of keratin materials comprising applying compositions of the present invention to the keratin materials in an amount sufficient to treat, care for, make-up and/or enhance the appearance of the keratin materials are provided.

In accordance with all of the foregoing embodiments of the present invention, the compositions of the present invention may be applied to keratin materials as needed, preferably once or twice daily, more preferably once daily and then preferably allowed to dry before subjecting to contact such as with clothing or other objects.

According to yet other embodiments of the present invention, methods of producing a composition such as, for example, a mascara composition at or about room temperature comprising combining at least one cross-linked starch and at least one bimodal film forming agent are provided.

The present invention also envisages kits and/or prepackaged materials suitable for consumer use containing one or more compositions according to the description herein (for example, kits containing (1) a composition for application to keratin material such as mascara, eyeliner, eyeshadow, a lip composition such as liquid lip color, foundation, etc.; and (2) a basecoat and/or topcoat). Such kits may also include other compositions or components such as, for example, a cosmetic removing composition, instructions for applying or using the compositions in the kit, cosmetic application devices (for example, a mascara brush), etc.

The packaging and application device for any subject of the invention may be chosen and manufactured by persons skilled in the art on the basis of their general knowledge, and adapted according to the nature of the composition to be packaged. Indeed, the type of device to be used can be in particular linked to the consistency of the composition, in particular to its viscosity; it can also depend on the nature of the constituents present in the composition, such as the presence of volatile compounds.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLE 1

Mascara

| INCI NAME | % |
| --- | --- |
| Syntran PC 5100 | 74.50 |
| CosmetaGem from Glitterex | 8.00 |
| 100μ Polyester Jewel Silver | 3.20 |
| 150μ Polyester Jewel Silver | 0.80 |
| Butylene Glycol | 10.00 |
| Structure XL | 3.50 |
| TOTAL | 100.00 |

Procedure
1. Syntran and glitters were combined in beaker with lightning mixer until glitters are fully dispersed.
2. Butylene glycol was added and mixing was continued.
3. Structure XL was slowly added and mixing speed was increased to incorporate completely (15 mins).

Drop batch after it was homogenously thickened.

EXAMPLE 2

Mascara

Wax-Free Lash Gel Mascara

| Phase | INCI NAME | % |
| --- | --- | --- |
| A | Structure XL | 4.50 |
|   | D.I. Water | 15 |
| B | Nanosperse Ink Black PV aq | 20 |
| C | Syntran PC 5100 | 56.00 |
|   | Butylene Glycol | 4.00 |
|   | Phenoxyethanol | 0.50 |
|   | TOTAL | 100.00 |

Procedure
1. Phase A (D.I. water & Structure XL) was combined in beaker with lightning mixer (5 mins).
2. Phase B (Nanosperse Ink Black PV aq) was added at R.T. and mixing was continued, making sure to scrape from the sides of the beaker as the mixture thickened (15 mins).
3. In separate beaker, Phase C (Syntran 5100, butylene glycol & preservative) was combined at R.T with mixing, and was immediately added to Phases A & B.
4. Mixing was continued until smooth and creamy (20 mins).

EXAMPLE 3

Mascara

| Phase | INCI NAME | % |
| --- | --- | --- |
| A | Syntran PC 5100 | 74.00 |
|   | Cosmetagem Coated Black (.006) Hex | 8.00 |
|   | Poly*Flake Coated Silver (.004) Hex | 4.00 |
| B | Butylene Glycol | 10.00 |
| C | Phenoxyethanol | 0.50 |
| D | Structure XL | 3.50 |
|   | TOTAL | 100.00 |

Procedure
1. Syntran and glitters were combined in beaker with lightning mixer until glitters were fully dispersed.
2. Butylene glycol and phenoxyethanol were added and mixing was continued.
3. Structure XL was slowly added and mixing speed was increased to incorporate completely (15 mins).

Drop batch after it was homogenously thickened.

EXAMPLE 4

| Phase | INCI NAME | % |
| --- | --- | --- |
| A | D.I. Water | 34 |
|   | Structure XL | 6.00 |
| B | Syntran PC 5100 | 34.00 |
|   | Nanosperse Ink Black PV aq | 16 |
| C | Butylene Glycol | 9.10 |
| D | Liquapar Optima | 0.90 |
|   | TOTAL | 100.00 |

Procedure
1. Phase A ingredients were combined in beaker with lightning mixer until homogeneous and smooth (15 mins).
2. Phase B was added and mixed until fully incorporated (15 mins).
3. Phases C & D were added and mixed (5 mins each).

EXAMPLE 5

| Phase | INCI NAME | % |
| --- | --- | --- |
| A | D.I. Water | 34 |
|   | Structure XL | 6.00 |
| B | Syntran PC 5100 | 21.00 |
|   | Syntran PC 5208 | 13.00 |
|   | Nanosperse Ink Black PV aq | 16 |
| C | Butylene Glycol | 9.10 |
| D | Liquapar Optima | 0.90 |
|   | TOTAL | 100.00 |

Procedure
1. Phase A ingredients were combined in beaker with lightning mixer until homogeneous and smooth (15 mins).

2. Phase B was added and mixed until fully incorporated (15 mins).
3. Phases C & D were added and mixed (5 mins each).

What is claimed is:

1. A composition comprising:
   at least one cross-linked starch selected from the group consisting of a crosslinked product of a hydroxyalkyl modified starch with a carbon number of 2 to 5, a crosslinked product of a hydroxyalkyl modified starch with a carbon number of 2 to 5 and an acyl modified starch with a carbon number of 2 to 18, and a crosslinked product of an acyl modified starch with a carbon number of 2 to 18; and
   at least one bimodal polymer comprising at least one monomer selected from the group consisting of an acrylic acid-based monomer, a (meth)acrylic acid-based monomer, an acrylate-based monomer, and a (meth)acrylate-based monomer, and having at least one cationic functionality and at least one anionic functionality;
   wherein the composition is not in the form of an emulsion.

2. The composition according to claim 1, wherein the content of the at least one bimodal polymer is from about 15% to about 80% by weight with respect to the total weight of the composition.

3. The composition according to claim 1, wherein the content of the at least one bimodal polymer is from about 30% to about 70% by weight with respect to the total weight of the composition.

4. The composition according to claim 1, wherein the content of the at least one bimodal polymer is from about 50% to about 70% by weight with respect to the total weight of the composition.

5. The composition according to claim 1, wherein the content of the at least one cross-linked starch is from about 1% to about 15% by weight with respect to the total weight of the composition.

6. The composition according to claim 4, further comprising from about 1% to about 15% by weight with respect to the total weight of the composition of the at least one cross-linked starch.

7. The composition according to claim 1, wherein the composition is substantially wax-free.

8. The composition according to claim 1, wherein the composition is wax-free.

9. The composition according to claim 4, wherein the composition is substantially wax-free.

10. The composition according to claim 4, wherein the composition is wax-free.

11. The composition according to claim 1, wherein the composition is a mascara, eyeliner or eyeshadow.

12. The composition according to claim 4, wherein the composition is a mascara, eyeliner or eyeshadow.

13. The composition according to claim 6, wherein the composition is a mascara, eyeliner or eyeshadow.

14. The composition according to claim 1, further comprising glitter.

15. A method of adhering glitter to eyelashes comprising applying a composition to the eyelashes, wherein the composition comprises glitter,
   at least one cross-linked starch selected from the group consisting of a crosslinked product of a hydroxyalkyl modified starch with a carbon number of 2 to 5, a crosslinked product of a hydroxyalkyl modified starch with a carbon number of 2 to 5 and an acyl modified starch with a carbon number of 2 to 18, and a crosslinked product of an acyl modified starch with a carbon number of 2 to 18; and
   at least one bimodal polymer comprising at least one monomer selected from the group consisting of an acrylic acid-based monomer, a (meth)acrylic acid-based monomer, an acrylate-based monomer, and a (meth)acrylate-based monomer, and having at least one cationic functionality and at least one anionic functionality;
   wherein the composition is not in the form of an emulsion.

16. A method of curling or lifting eyelashes comprising applying a composition in an amount sufficient to curl or lift the eyelashes, wherein the composition comprises:
   at least one cross-linked starch selected from the group consisting of a crosslinked product of a hydroxyalkyl modified starch with a carbon number of 2 to 5, a crosslinked product of a hydroxyalkyl modified starch with a carbon number of 2 to 5 and an acyl modified starch with a carbon number of 2 to 18, and a crosslinked product of an acyl modified starch with a carbon number of 2 to 18; and
   at least one bimodal polymer comprising at least one monomer selected from the group consisting of an acrylic acid-based monomer, a (meth)acrylic acid-based monomer, an acrylate-based monomer, and a (meth)acrylate-based monomer, and having at least one cationic functionality and at least one anionic functionality;
   wherein the composition is not in the form of an emulsion.

17. A kit comprising (a) a mascara comprising at least one cross-linked starch selected from the group consisting of a crosslinked product of a hydroxyalkyl modified starch with a carbon number of 2 to 5, a crosslinked product of a hydroxyalkyl modified starch with a carbon number of 2 to 5 and an acyl modified starch with a carbon number of 2 to 18, and a crosslinked product of an acyl modified starch with a carbon number of 2 to 18; and
   at least one bimodal polymer comprising at least one monomer selected from the group consisting of an acrylic acid-based monomer, a (meth)acrylic acid-based monomer, an acrylate-based monomer, and a (meth)acrylate-based monomer, and having at least one cationic functionality and at least one anionic functionality;
   and (b) a basecoat composition or a topcoat composition;
   wherein the mascara composition is not in the form of an emulsion.

* * * * *